United States Patent [19]

Papantonakos

[11] Patent Number: 4,895,560
[45] Date of Patent: Jan. 23, 1990

[54] ANGIOPLASTY APPARATUS

[76] Inventor: Apostolos C. Papantonakos, 10, Korizi Str. - Kalamki, Athens, Greece

[21] Appl. No.: 176,365

[22] Filed: Mar. 31, 1988

[51] Int. Cl.$^4$ ............................................. A61B 17/32
[52] U.S. Cl. ..................................... 604/22; 606/159
[58] Field of Search ................. 604/22; 128/304, 305, 128/343, 344, 751–755

[56] References Cited

U.S. PATENT DOCUMENTS

| | | |
|---|---|---|
| 396,754 | 1/1889 | Mayfield . |
| 958,854 | 5/1910 | Bunn . |
| 1,112,982 | 10/1914 | Conine . |
| 2,328,199 | 8/1943 | Day . |
| 3,732,858 | 5/1973 | Banko . |
| 3,906,954 | 9/1975 | Baehr et al. . |
| 4,228,802 | 10/1980 | Trott . |
| 4,273,128 | 6/1981 | Lary . |
| 4,445,509 | 5/1984 | Auth . |
| 4,625,712 | 12/1986 | Wampler . |
| 4,665,914 | 5/1987 | Tanne ................................. 128/305 |
| 4,717,381 | 1/1988 | Papantonakos . |
| 4,729,763 | 3/1988 | Henrie ................................. 128/305 |
| 4,784,636 | 11/1988 | Rydell ................................. 604/22 |

FOREIGN PATENT DOCUMENTS 0297020 12/1988 European Pat. Off. .

Primary Examiner—Michael H. Thaler
Assistant Examiner—William Lewis
Attorney, Agent, or Firm—Fleit, Jacobson, Cohn, Price, Holman & Stern

[57] ABSTRACT

An angioplasty apparatus for removing abnormal deposits such as atheromatic plaque from the interior coronary or peripheric arterial walls and the like is provided. The apparatus includes an elongate hollow outer tube for insertion into an arterial vessel. A rotatable driving rod is engaged with the tube and extends forwardly into the arterial vessel. An actuator is provided in the tube for rotating the driving rod alternately in opposite directions. A milling tool having milling flutes is coupled to the driving rod exterior to the tube and mills the deposits when the milling tool is rotated and brought into contact with the abnormal deposits. The apparatus also includes an electrical sensor for determining when the deposit has been removed from the arterial walls in order to preserve existing healthy arterial wall tissue and a suction device in communication with the tube for withdrawing the milled micro-particles of the abnormal deposits from the arterial vessel.

16 Claims, 13 Drawing Sheets

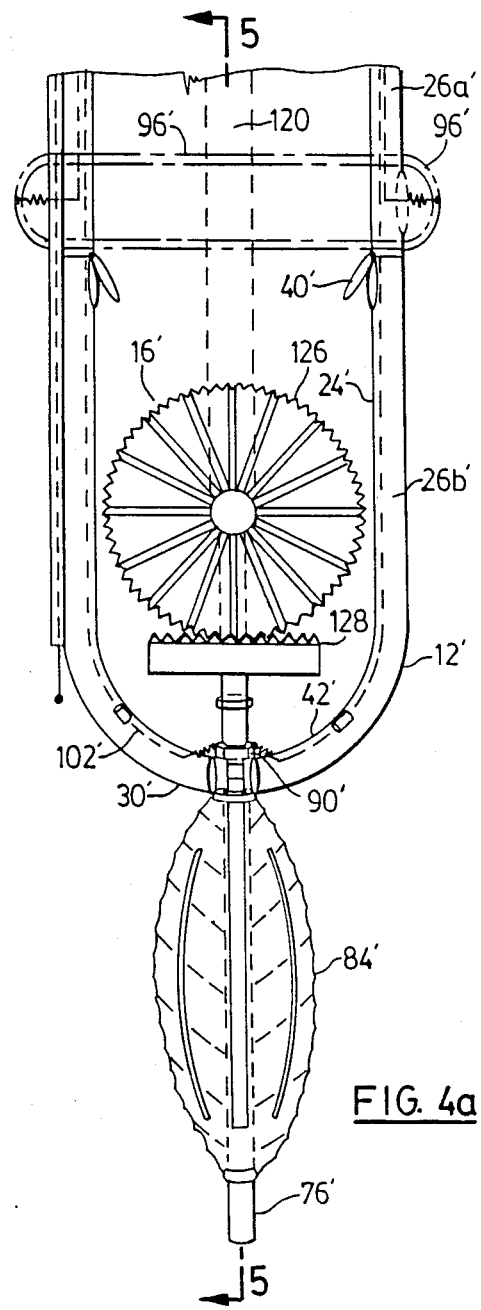
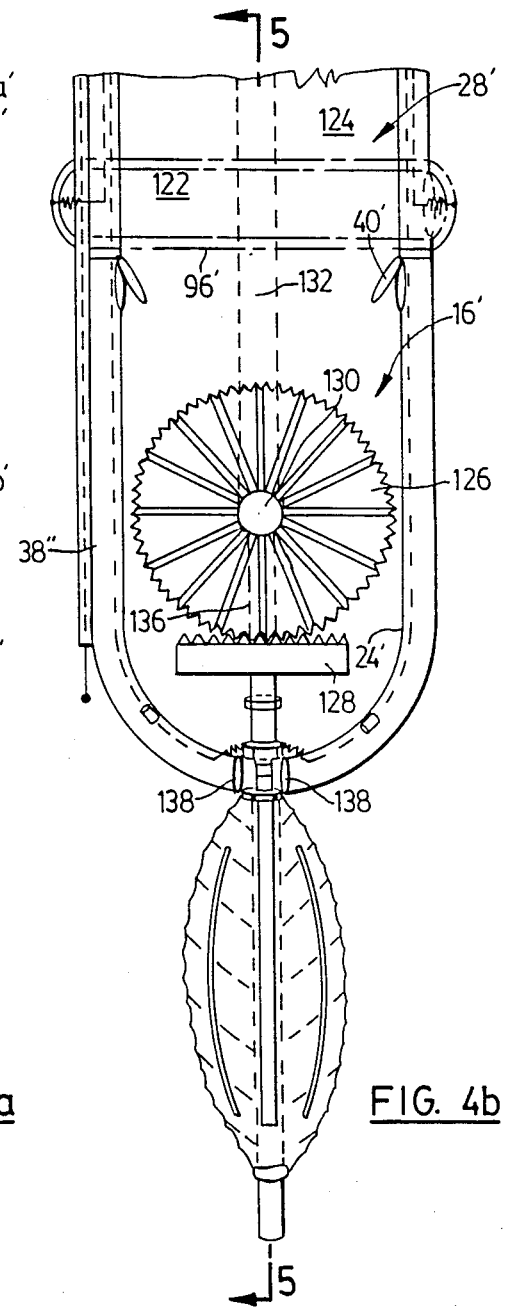
FIG. 4a
FIG. 4b

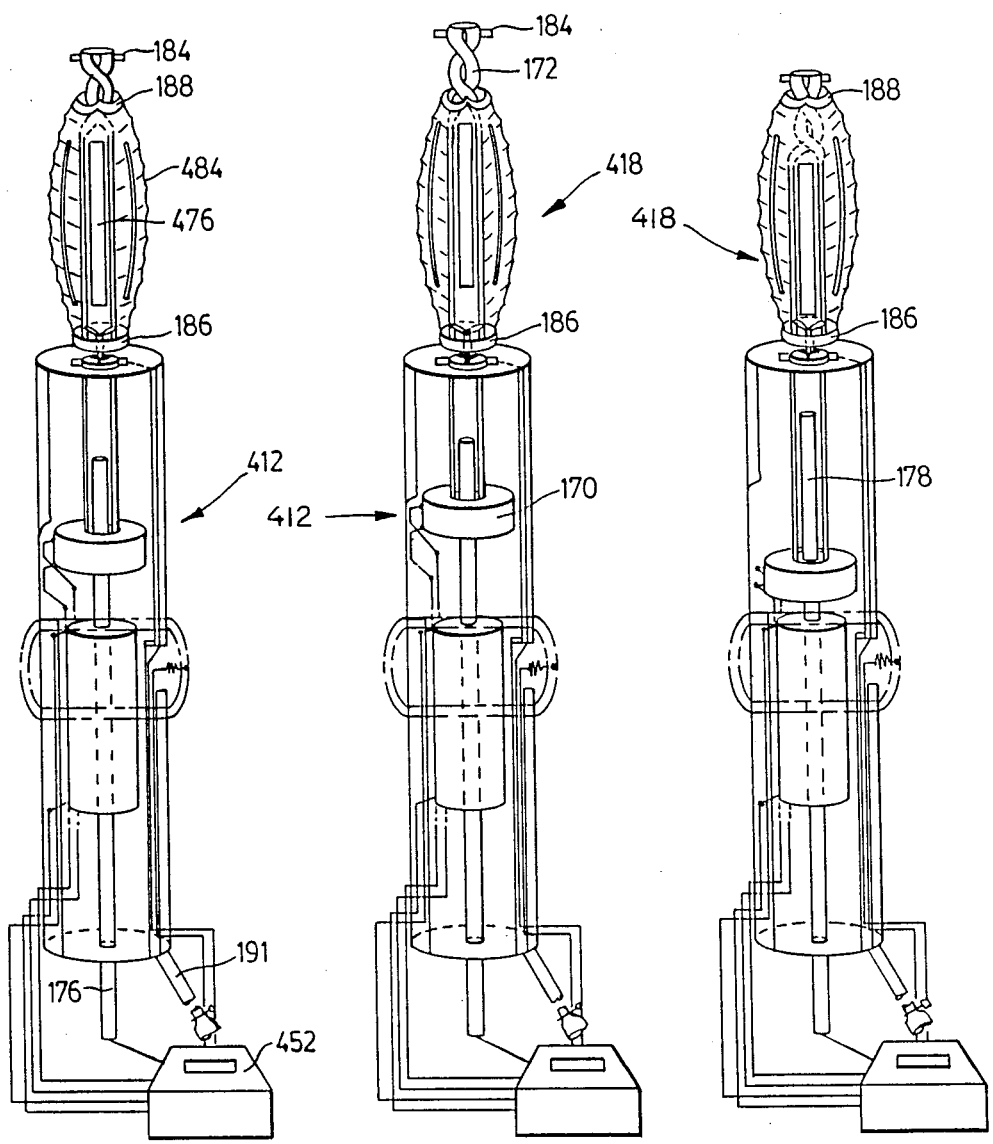

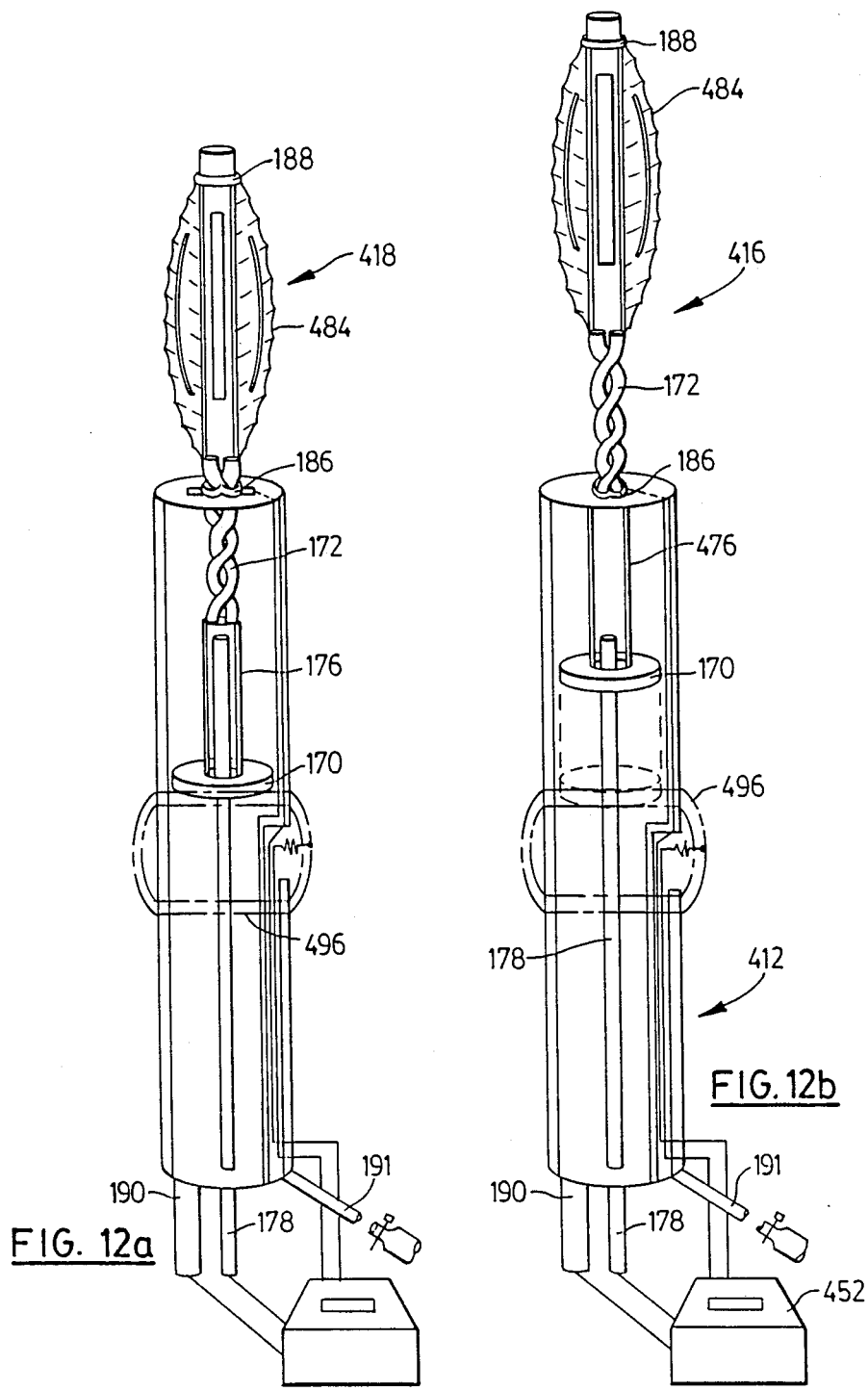

ANGIOPLASTY APPARATUS

The present invention relates to an angioplasty apparatus for removing abnormal deposits from interior coronary or peripheric arterial walls and the like.

Devices for removing abnormal deposits from arterial walls in the human body are known in the art. In particular, U.S. Pat. No. 4,445,509 to Auth shows a method and apparatus for the removal of abnormal deposits from the interior walls of a blood vessel. The Auth device includes an elliptical cutting tool mounted at one end of a hollow flexible rotating drive shaft that extend sinto a catheter. When the catheter and cutting tool are inserted into the blood vessel, the cutting tool is rotated by an actuator which is located exterior to the catheter and coupled to the other end of the drive shaft. Cutting flutes are provided on the cutting tool for engaging with and cutting tissue to remove it from the vessel walls. The cut particles of the deposit are withdrawn from the blood vessel through radial ports providedin the cutting tool and into the hollow shaft by way of a suction device.

The Auth device operates on the principle of cutting materials with different physical characateristics and implements a high speed rotating cutting tool. In desired operation, the soft vessel tissue when contacted with the spinning cutting flutes deforms under the force and thus, is not damaged. However, the more rigid deposit tissue is cut under contact with the flutes.

However, a number of problems exist in the Auth device. Since the flexible drive shaft is not provided with means for locating and securing it in the vessel, the cutting tool is able to move with respect to the deposit, thereby reducing the effectiveness of the device. Also, since the shape of the cutting tool is fixed, the device cannot operate effectively in various size vessels. Moreover, since the Auth device relies on the healthy vessel tissue deforming under contact with the cutting tool, damage can often occur to the healthy vessel tissue. Accordingly, there is a need for an improved angioplasty apparatus for removing abnormal deposits from the interior walls of blood vessels and the like.

It is an object of the present invention to obviate or mitigate the above disadvantages.

According to the present invention there is provided an angioplasty apparatus for removing abnormal deposits such as atheromatic plaque from the interior walls of blood vessles and the like comprising:

a hollow elongate flexible member having one end for insertion into said vessel;

a driving member coupled at one end to said elongate member and extending forwardly at the other end into a vessel;

milling means coupled to a driving member exterior to said elongate flexible member;

drive means in communication with said driving member for actuating said driving member, said driving member rotating said milling means alternately in opposite directions to engage and mill said deposits upon actuation thereof by said drive means;

suction means in communication with said elongate flexible member for withdrawing milled particles of said deposit from said vessel and into said elongated flexible member ; and sensing means located on said elongate flexible member and being for coupling between said vessel and said milling means for sensing when said milling means has removed said deposit from, the interior walls of said vessel.

Preferably, the sensing means comprises a potential voltage source, a current comparator and a pair of resistive circuits for the electrical resistance between a healthy arterial section of vessel tissue and that of the tissue contacted by the milling means.

Preferably, the milling means is a flexible leaf-shaped milling tool provided with shallow milling flutes to reduce greatly the occurrence of damage to the vessel tissue underlying the deposit to be removed. It is also preferred that the apparatus includes an inflatable member for securing the flexible member in position in the blood vessel.

Preferably, the elongate member is linearly displaceable with respect to the driving member in order to impart a force on the flexible milling tool to cause a change in the radial dimension of the milling tool. This allows the apparatus to operate effectively in various size arterial branches and to remove atheromatic deposits of different sizes.

It is also preferred that the angioplasty apparatus further includes a linear displacement means disposed on the other end of the driving member to allow the millingmeans to be displaced linearly therealong while still being rotated alternately in opposite directions. In this manner, a large deposit in a vessel can be removed without requiring the milling means to be repositioned in the vessel.

The present apparatus provides the advantages of allowing large deposits to be removed effectively and safety from blood vessels without frequent repositioning of the apparatus in the vessel. Furthermore, the sensing means, the inflatable member and the shallow cutting flutes provided on milling means allow the apparatus to remove the abnormal deposits of various sizes from various size blood vessels while greatly reducing the occurrence of damage to the vessels.

Embodiments of the present invention will now be described by way of example only with reference to the accompanying drawings in which:

FIGS. 4a and 4b are partial perspective sectional views of one end of another angioplasty apparatus;

Figures 5A, 5B:
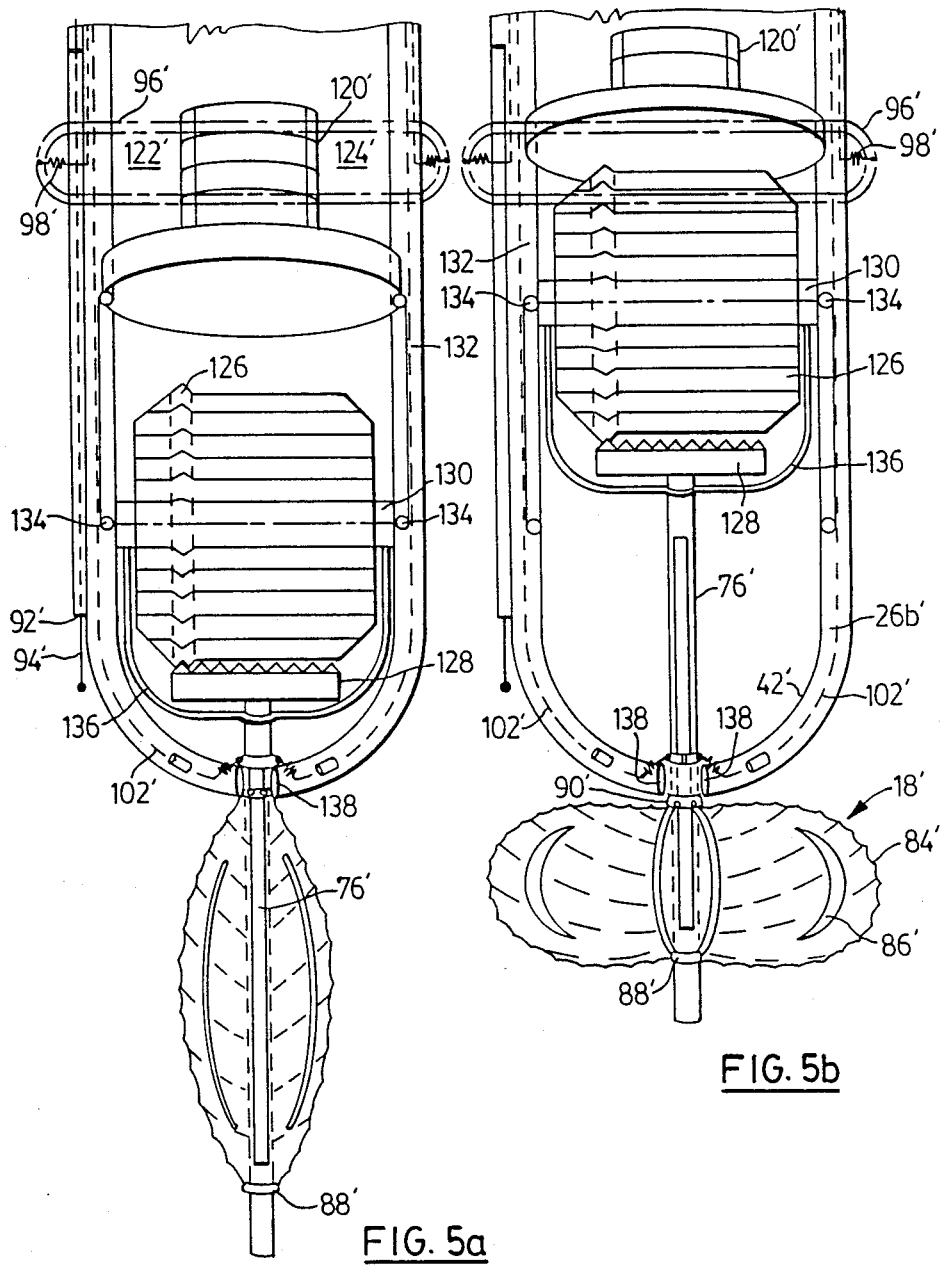
Figure 6:
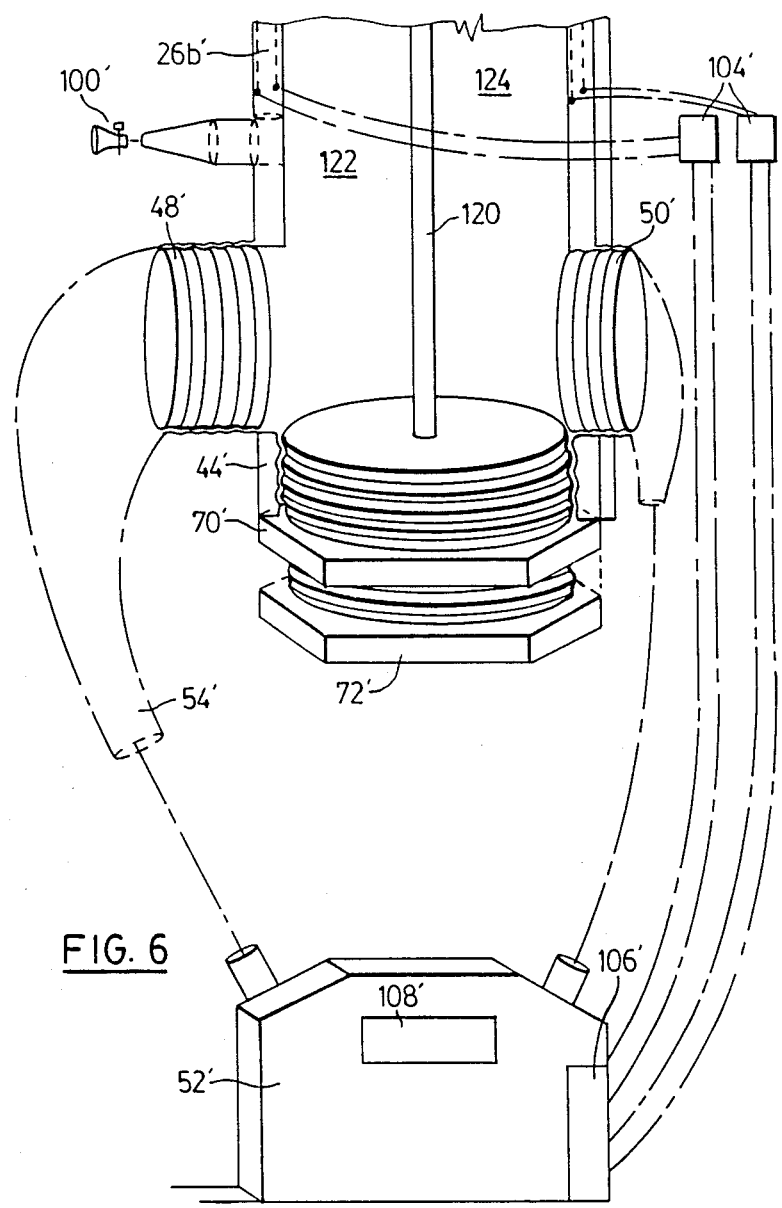
Figures 7A, 7B:
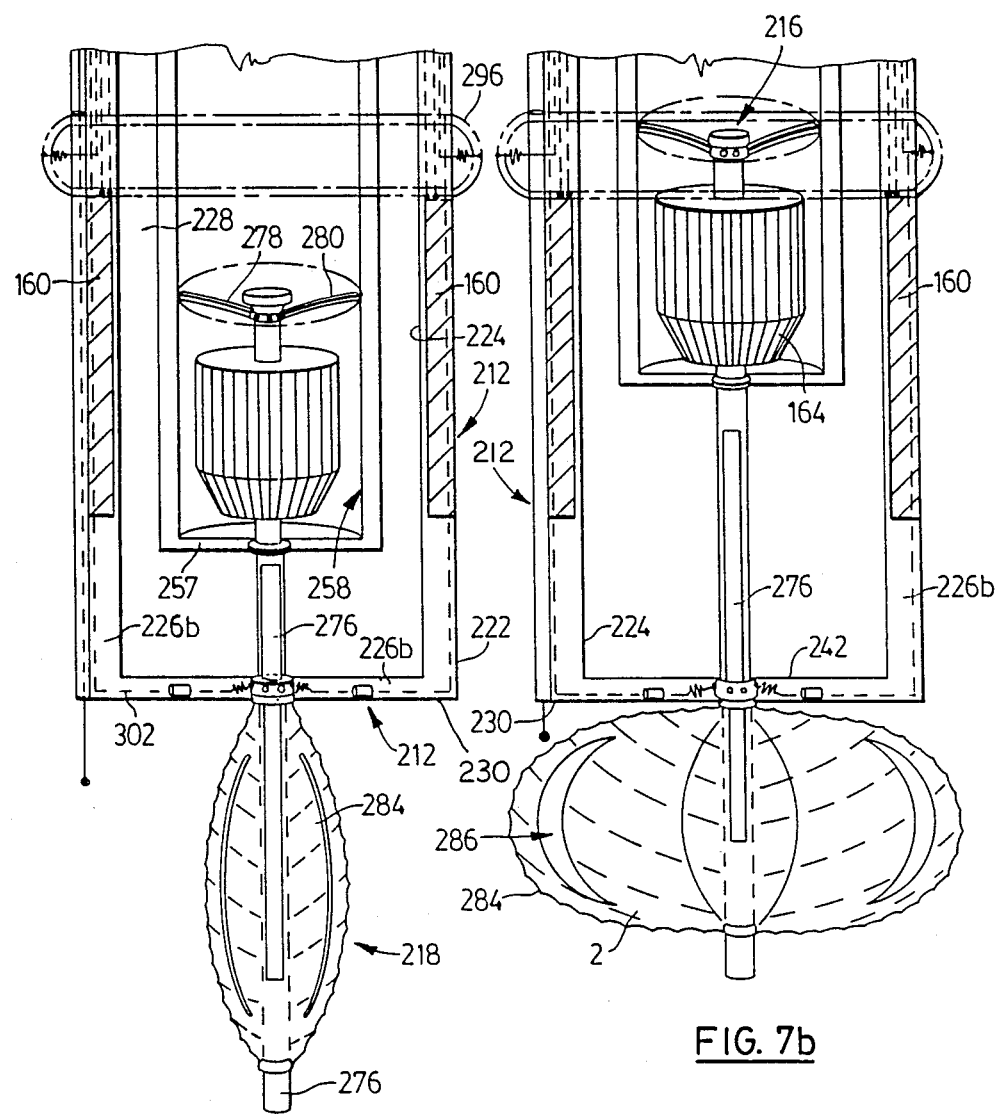
Figures 8A, 8B, 8C:
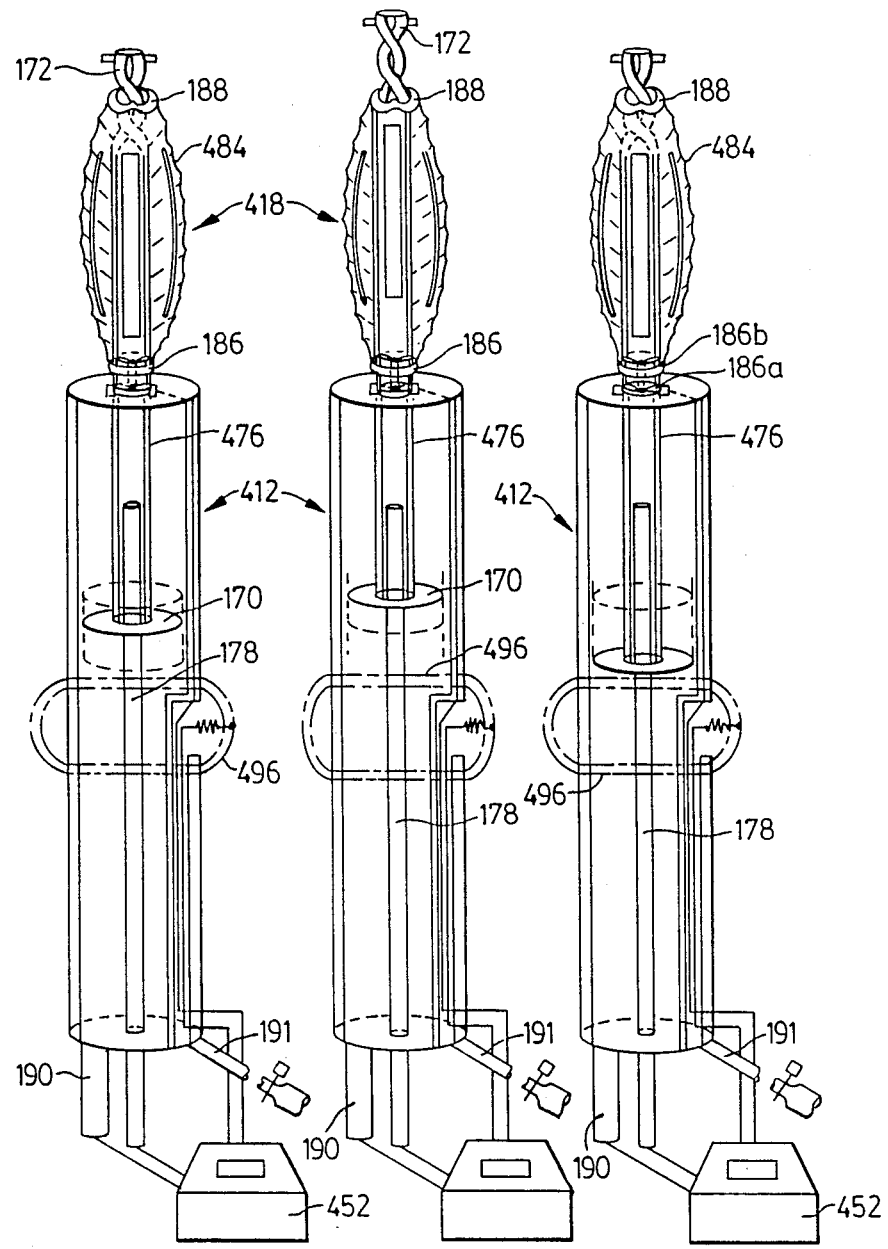
Figure 10A:
Figure 10B:
Figure 10D:
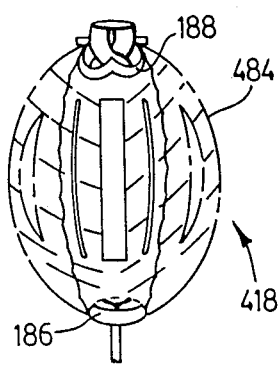
Figure 10E:
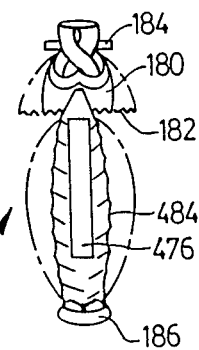
Figure 10C:
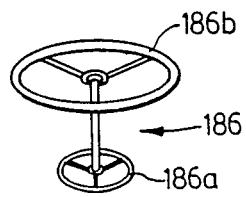
Figure 10F:
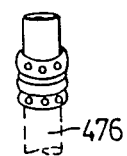
Figure 11A:
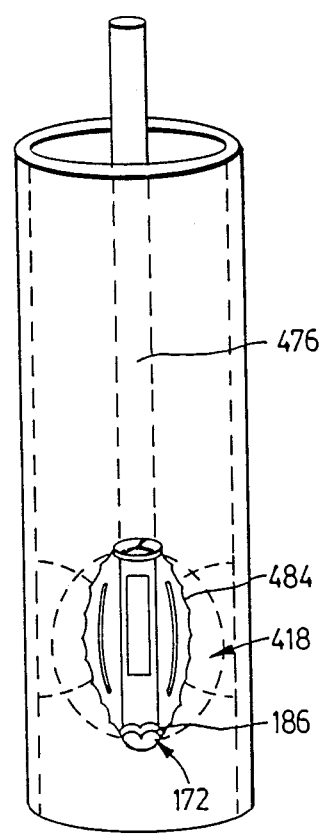
Figure 11B:
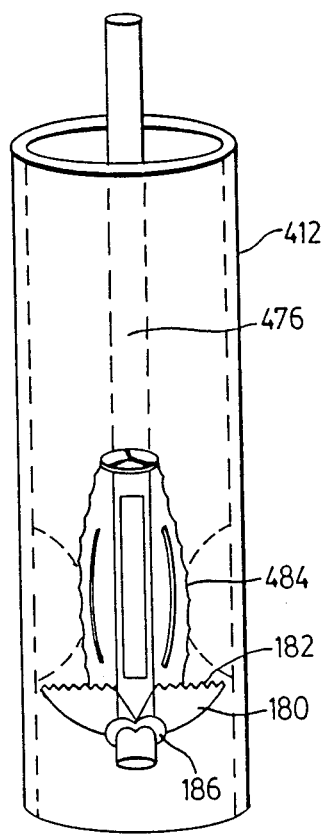
Figures 13A, 13B:
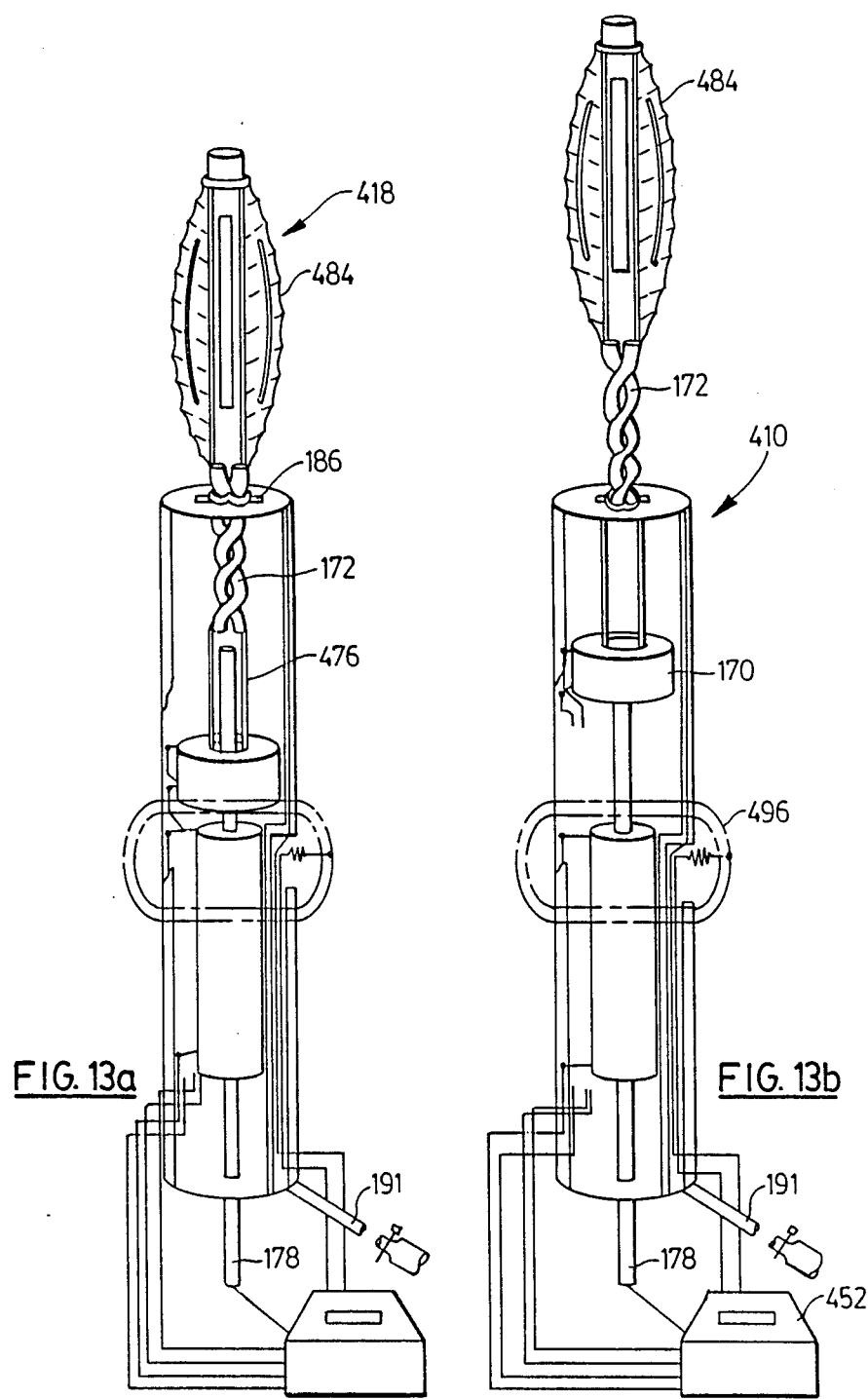

FIGS. 5a and 5b are partial perspective sectional views of FIGS. 4a and 4b taken along lines 5—5;

FIG. 6 is a partial perspective sectional view of another portion of the other end of the apparatuses illustrated in FIGS. 4 and 5;

FIGS. 7a and 7b are partial perspective sectional views of one end of still yet other angioplasty apparatuses;

FIGS. 8a, 8b and 8c are partial perspective sectional views of other angioplasty apparatuses;

FIGS. 9a, 9b and 9c are partial perspective sectional views of still yet other angioplasty apparatuses;

FIGS. 10a, 10b, 10c, 10d, 10eand 10f are partial perspective views of portions of the apparatuses illustrated in FIGS. 8 and 9;

FIGS. 11a and 11b are partial perspective views of the apparatuses illustrated in FIGS. 8 and 9 in operation;

FIGS. 12a and 12b are perspective views of still yet other angioplasty apparatuses; and FIGS. 13a and 13b are perspective views of still yet other angioplasty apparatuses.

Figure 1:
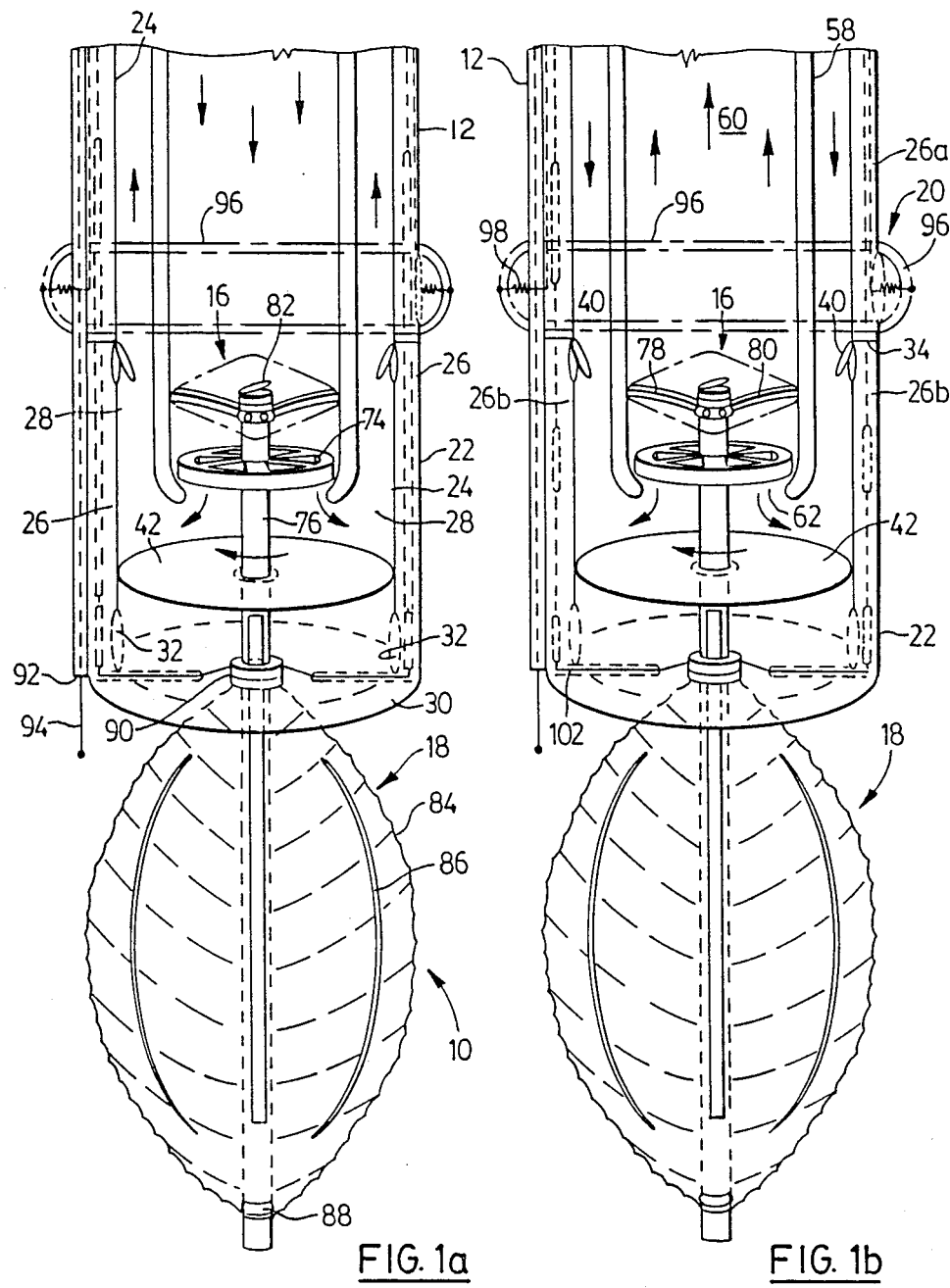
FIGS. 1a and 1b are partial perspective sectional views of one end of an angioplasty apparatus.
Figure 2:
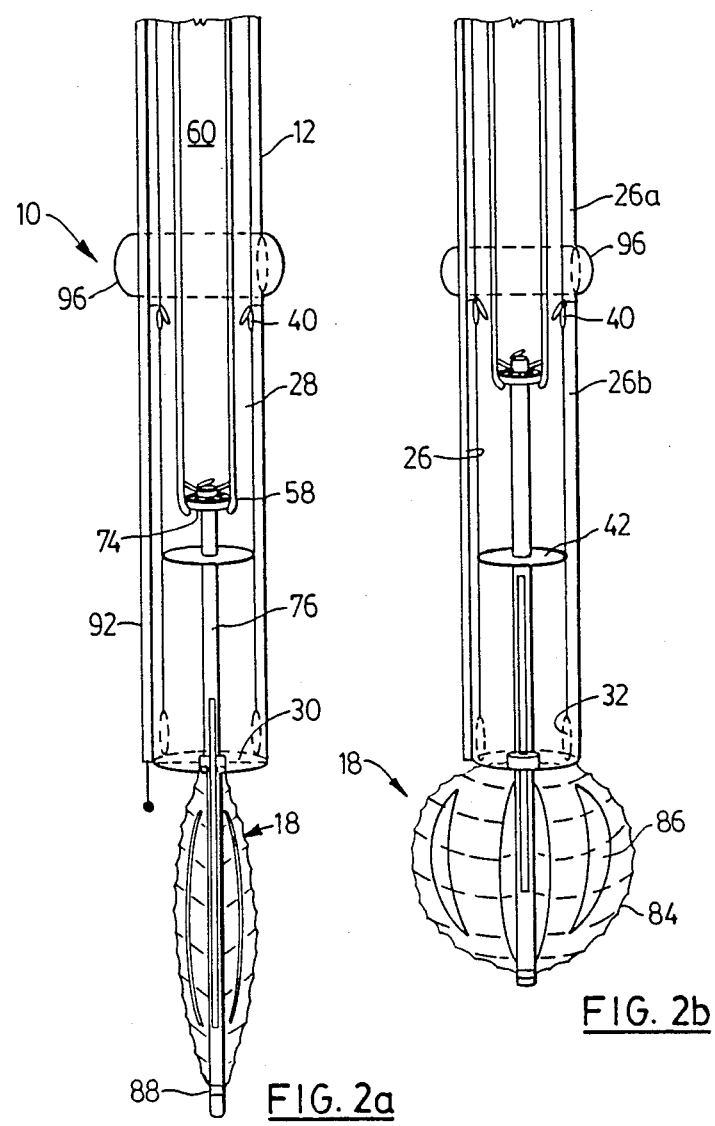
FIGS. 2a and 2b are partial perspective sectional views of the one end illustrated in FIGS. 1a and 1b in operation.
Figure 3:
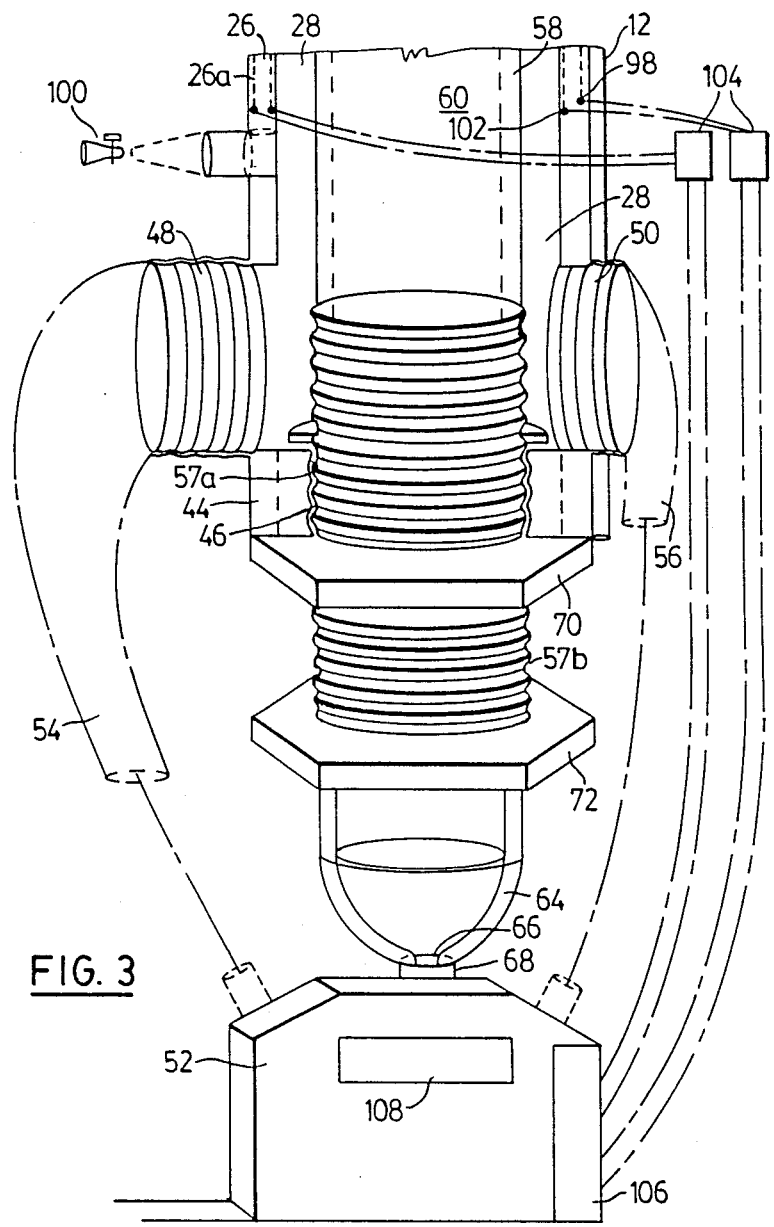
FIG. 3 is a partial perspective sectional view of the other end of an angioplasty apparatus.

Referring to FIGS. 1, 2 and 3, an angioplasty apparatus 10 is shown. The apparatus includes an elongate cylindrical flexible hollow plastic outer tube 12 for insertion into a blood vessel (not shown). A drive mechanism 16 is provided to rotate a milling tool 18 alternatively in opposite directions in order to remove abnormal deposits (not shown) from the walls of the vessel. A sensing device 20 is also provided for detecting when the abnormal deposit has been removed from the vessel by comparing the electrical resistance of healthy arterial tissue with that of the tissue contacted by the milling tool 18.

The outer tube 12 includes an outer wall 22 and an inner wall 24 defining outer and inner passages 26 and 28 respectively. A base plate 30 is sealed on one end of the outer tube and has a central bore provided therein for allowing the driving mechanism 16 to extend beyond the end of the outer tube 12 and into the vessel. The inner wall 24 has a portion of its structure removed proximal to the base plate 30 to provide an opening 32 between the inner passage 28 and the outer passage 26. A plate 34 is positioned in the outer passage 26 and is tightly sealed between the inner and outer walls 24 and 22 to divide the outer passage 26 into upper and lower portions 26a and 26b respectively. An annular valve 40 moveable between opened and closed positions is located adjacent the plate 34 on opposite sides of the inner wall 24 of the lower portion 26b, to provide a second path from the outer passage 26 to the inner passage 28.

A circular isolating plate 42 is located in the inner passage 28 near the base plate 30 and is tightly sealed to the inner wall 24. The isolating plate 42 is also provided with a central bore in alignment with the bore provided in the base plate 30.

The other end of the inner and outer walls 22 and 24 are sealed to form an annular shoulder 44. Drainage tubes 48 and 50 outwardly extend from the inner passage 28 to the exterior of the outer tube 12 to provide a path from the inner passage 28 to the exterior of the outer tube 12. The drainage tubes 48 and 50 are also connected to a forced air supply controller 52 by connector hoses 54 and 56.

The other end of the inner wall 24 is also provided with threads 57a for mating engagement with the threads 57b provided on a cylindrical hollow plastic inner tube 58. The inner tube 58 extends into the inner passage 28 thereby defining a central passage 60. The end of the inner tube 58 extending into the outer tube 12 terminates inwardly to form an opening 62 having a diameter less than that of the central passage 60. The other end of the inner tube 58 extending beyond the shoulder 44 terminates in a semi-spherical end section 64. The section 64 is provided with an aperture 66 and is coupled to the controller 52 by a connector hose 68. A pair of nuts 70 and 72 are also provided. The nut 70 is secured to the shoulder 44 and the nut 72 is secured in position on the threads of the inner tube 58. The threads 57a and 57b allow the inner tube 58 to be displaced linearly with respect to the outer tube 12 as well be described.

The driving mechanism 16 is preferably formed from lightweight plastic components and includes a turbine 74 located near the inner end of the inner tube 58. The turbine 74 is formed having a diameter slightly less than the diameter of the central passage 60 but greater than the diameter of the opening 62. The turbine 74 is connected to an elongate hollow driving rod 76 extending through the bores provided in the isolating plate 42 and the base plate 30 and out into the vessel. The driving rod 76 also extends upwardly into the central passage 60 beyond the turbine 74 and is rotatably coupled to three anchors, two 78 and 80 of which are shown. The anchors are spaced by 120° and are secured to the inner tube 58, to permit rotational movement of the driving rod 76 while inhibiting linear movement thereof. The end of the hollow driving rod 76 positioned in the central passage 60 is provided with a closure flap 82 moveable between open and closed positions.

The milling tool 18 is secured to the driving rod 76 exterior to the tube 12 and is flexible and leaf-shaped. Preferably, the tool 18 is formed from stainless steel and includes shallow milling flutes 84 and airing slots 86. The distal end of the milling tool 18 is secured to the driving rod 76 by a coupling 88. The other end of the milling tool 18 is slidably engaged with the driving rod 76 by a second coupling 90. The second coupling 90 is dimensioned so that it is not capable of passing through the central bore of the base plate 30. The driving rod 76 also has a portion of its structure removed extending from inside the outer tube 12 to the coupling 88 to allow milled particles of the deposits to be removed from the vessel into the apparatus 10 by suction.

One side of the outer tube 12 is provided with a guiding tube 92 for supporting a guiding wire 94. The guiding tube and wire aid in the placement of the apparatus 10 in the vessel. The outer tube 12 is also surrounded by an inflatable balloon 96 which contacts a healthy arterial vessel wall section when inflated to secure the apparatus 10 in the vessel. A valve 100 positioned near the shoulder 44 allows air or a saline solution to be infused into the upper portion 26a of the outer passage 26 so that the balloon 96 can be inflated.

The sensing device 20 includes first resistive wires 98 which are coupled at one end to opposite ends of the balloon 96 and second resistive wires 102 which are coupled at one end to the coupling 90. The other end of the first and second resistive wires 98 and 102 respectively are coupled to potential voltage sources 104 which in turn are connected to the controller 52. The controller 52 also includes a comparator 106 and an indicator 108 operable to detect and inform the operator when the abnormal deposit has been removed.

In operation of the angioplasty apparatus 10, the outer tube 12 is inserted into the vessel so that the milling tool 18 is positioned near the deposit to be removed. Thereafter, the balloon 96 is inflated with the air or saline solution via the valves 100 and the upper portion 26a to secure the apparatus 10 in the vessel and to bring the resistive wires 98 into contact with the healthy arterial vessel wall section. Following this, air is pumped into the central passage 60 of the inner tube 58 via the controller 52 and connector hose 68 and is forced downwardly towards the turbine 74. The turbine 74 which is securely affixed to the driving rod 76, rotates when the forced air passes therethrough and translates the rotational motion to the driving rod 76 and hence, the milling tool 18. The forced air is recirculated to the controller 52 via the inner passage 28, the drainage tubes 48 and 50 and the connector hoses 54 and 56.

As the milling tool 18 is rotated, it contacts and mills the abnormal deposits located on the inner wall of the vessel since the deposit tissue does not deform under contact with the milling flutes 84 due to its rigidity. The milled particles of the deposit are drawn into the removed structure of the driving rod 76 due to the pressure differential in the vessel caused by the rotation of the milling tool 18 and the negative pressure created in the passageways 28 and 60 due to the air flow. The milled particles are forced upwardly through the driving rod 76 into the lower portion of the outer tube 12 defined by the isolating plate 42 and the base plate 30. The particles are then drawn through the opening 32 and pass upwardly through the lower portion 26b of the outer passage 26.

The particles are then drawn into the inner passage 28 through the valve 40 which is held open by the recirculating air flowing in the inner passage 28. The particle and recirculating air mixture is conveyed to the controller 52 as previously described and the mixture is filtered to remove the particles before the air is recirculated into the central passage 60.

When it is desired to reverse the direction of rotation of the milling tool 18, air is supplied into the inner passage 28 via the connector hoses 54 and 56 and drainage tubes 48 and 50 as opposed to the central passage 60. Thus, the air is forced downwardly into the inner passage 28 and passes upwardly through the turbine 74 into the central passage 60. The return air flow in the central passage 60 is conveyed to the controller 52 via the connector hose 68. The passage of air upwardly through the turbine 74 causes it to rotate in a direction opposite to that as previously described.

The rotation of the turbine 74 in the opposite direction causes the driving rod 76 and hence, the milling tool 18 to rotate to contact and mill the deposits. Similarly, the rotation of the milling tool 18 forces the milled particles to be drawn into the removed structure of the driving rod 76. However, since the upward force generated by the rotation of the milling tool 18 acts to open the closure flap 82 and since the air passing through the central passage 60 flows in the same direction as the upward force, the closure flap 82 opens, to allow the milled particles to pass into the central passage 60. Thus, the particles removed by the milling tool 18 are carried with the return flow of air in the central passage 60 and filtered from the air by the controller 52 before the air is recirculated. this design allows the milled particles withdrawn from the vessel to be filtered by the controller 52 without the particles contacting the turbine 74 regardless of the direction of rotation of the turbine. Furthermore, by alternating the direction of the air flow into and out of the passages 28 and 60, the milling tool 18 can be rotated alternately in opposite directions. This alternate rotational operation increases the effectiveness of the milling procedure.

To extend the edges of the milling tool 18 outwardly beyond the outer diameter of the outer tube 12, the nut 72 is rotated, thereby rotating the inner tube 58 to withdraw it from the outer tube. The resulting movement of the inner tube 58 acts to retract the driving rod 76 and milling tool 18 into the outer tube 12. The retraction of the milling tool 18 causes the coupling 90 to abut against the end plate 30 to prevent movement of the milling tool 18 into the outer tube 12. However, since the coupling 90 is slidable along the driving member, as the inner tube 58 is further withdrawn from the outer tube, the milling tool 18 is caused to expand in a direction perpendicular to the longitudinal axis of the apparatus. As the nut 72 is further rotated to withdraw the inner tube 58 from the outer lumen 12, the milling tool 18 is forced to expand further beyond the outer side of the outer tube 12. This allows the milling tool 18 to contact smaller deposits or opeate in wider arterial vessels. The second nut 70 is provided to set a limit for the release of the compressive forces placed on the milling tool 18 to ensure that the milling tool 18 is not permitted to resume a shape having a dimension which is inoperable for removing deposits from the vessel walls.

To sense when the deposit has been removed from the vessel walls, the voltage sources 104 located external to the outer tube 12 supply a potential voltage to the resistive wires 98 and 102. The comparator 106 monitors the currents flowing in each of the circuits 98 and 102 and compares the electrical resistance of the tissue contacted by the milling tool 18 with that of the healthy tissue contacted by the circuits 98. The presence of abnormal deposit tissue is detected, since the electrical resistance of the deposit tissue is greater than that of healthy arterial vessel tissue. When the abnormal deposit has been removed, the milling tool 18 will contact healthy tissue and hence, the monitored electrical resistance will be equal in both circuits 98 and 102 respectively. When this occurs, the comparator 106 inhibits operation of the controller 52 to prevent further milling in the vessel and provides an output to the indicator 108. The indicator in turn provides an to the user that the milling operation has been completed.

Referring now to FIGS. 4, 5 and 6, another angioplasty apparatus 10' is shown. In this embodiment, like reference numerals will be used to indicate like components with a '''''' added for clarity. In this embodiment, the inner wall 24 is not provided with an opening 32, but rather extends to the driving rod 76' to form the isolating plate 42'. The outer tube 12' is also provided with a divider 120 as opposed to an inner tube. The divider 120 positions the drive mechanism 16' and separates the inner passage 28' into a pair of parallel passages 122 and 124.

The drive mechanism 16' includes a pair of mating bevel gears 126 and 128. The first gear 126 is disposed on a shaft 130. Opposite ends of the shaft 130 are connected to members 132 viq gearings 134 and extend upwardly to engage with the divider 120. The ends of the shaft 130 are also coupled to the driving rod 76' via a support frame 136. The gear 126 is positioned to engage continuously with gear 128 and so that its axis of rotation is substantially perpendicular to the driving rod 76'.

The second gear 128 is secured to the driving rod 76' and aligned so that its axis of rotation is parallel to the longitudinal axis of driving rog 76'. The driving rod 76' similarly has a portion of its section removed, extending from the milling tool 18' to the exterior side of the isolating plate 42'. Apertures 138 are provided at the terminating ends of the lower portion 26b' of the outer passage 26' to provide a path for the milled particles from the vessel into the apparatus.

To rotate the milling tool 18', air is forced into one of passage 122 and recirculated through the other passage 124, thereby causing the gear 126 to rotate. The rotation of gear 126 in turn rotates gear 128 and hence, driving rod 76'. The milling tool 18' in turn is rotated, thereby allowing the deposits to be milled and hence, removed from the vessel. The milled particles of the deposit are drawn upwards through the driving rod 76' and into the other passage 124 by way of the apertures 138, lower portion 26b' of the outer passage 26' and the valve 40'. The particle and air mixture is conveyed to the controller 52' and the particles are filtered from the air in the manner previously described. To reverse the direction of rotation of the milling tool 18', the air is forced into the other passage 124 and recirculated through the one passage 122, thereby reversing the direction of rotation of the gears 126 and 128. As can be appreciated, by alternating the direction of air flow into the passages 122 and 124, the milling tool 18' can be rotated alternately in opposite directions.

Similar to the previous embodiment, the inner tube 58' and drive mechanism 16' can be displaced linearly with respect to the outer tube 12 to allow the flexible milling tool 18' to be compressed longitudinally so that the radial dimension of the milling tool increases. This is performed by rotating the nut 72' to withdraw the divider 120 from the outer tube 12' and in turn retract the drive mechanism 16' into the outer tube 12'. When this occurs the shaft 130 of the gear wheel 126 moves upwardly along the inner surface 24' via the bearings 134. The support frame 136 coupled between the shaft 130 and the driving rod 76' in turn moves the gear wheel 128 and the driving rod 76' in the same direction. Thus, in a similar manner, the milling tool 18' is compressed to extend its radial dimension.

As should be appreciated, the apparatus 10' of this embodiment is also positioned in the vessel via an inflatable balloon 96' and the removal of the deposit tissue is monitored by a sensing device 20' identical to that described previously.

FIGS. 7a and 7b show yet another embodiment of an angioplasty apparatus. Similarly, like reference numerals will be used to indicate like components with "200" added for clarity. In this embodiment the outer tube 212 is rectangular in shape and is provided with an integrally formed base plate 230. The plate 230 is provided with the central bore for the passage of the driving rod 276. The inner wall 224 is also sealed to the base plate 230, thereby sealing the lower portion 226b of outer passage 226 from the inner passage 228. Electromagnets 160 are provided in the lower portion 226b and surround the driving mechanism 216. The electromagnets are coupled to an AC power source (not shown) located in the controller for energizing the magnets 160. Provided in the outer tube 212 is a rectangular-shaped inner tube 258. A rotating magnetic rotor 164 is provided in the inner tube and is engaged with the driving rod 276. The inner tube 258 includes a base 259 having a control bore for allowing the driving rod 276 to extend beyond the base while sealing the lower end of the central passage 260, from the inner passage 228.

When the electromagnets 160 are energized via the power source, the rotor 164 is rotated in a direction dependent on the direction of the magnetic fields, thereby rotating the milling tool 218. Thus, the milling tool 218 rotates alternatively in opposite directions when energized with the AC supply voltage. The deposit material milled by the milling tool 218 is conveyed through the removed structure of the driving rod 276 and into the controller by way of the inner passage 228. The controller although not shown in this embodiment acts solely as a suction device since the rotation of the driving mechanism 216 is electrically powered and is not dependent on recirculating air.

It should be noted that the inner tube 258 can also be displaced linearly with respect to the outer tube 212 to expand the milling tool 218 in the same manner described for previous embodiments provided that the rotor 164 remains in the rotating field created by the electromagnets 160.

Referring now to FIGS. 8a to 8c, 10 and 11 still yet another angioplasty apparatus 410 is shown. In this embodiment, like reference numerals will be used to indicate like components with "400" added for clarity. The apparatus 410 uses as the drive mechanism 416, a piston 170 coupled to the driving rod 476. The hollow driving rod 476 terminates in a twisted wire pair 172 which permits bi-directional rotation of the milling tool 418. The piston 170 separates the inner passage 428 into lower and upper portions and is coupled on one side to the hollow driving rod 476. The driving rod 476 passes through the lower portion of the tube 412 to engage with the lower ring 186a of a coupling 186, the lower ring 186a is also being secured to the base 430. The milling tool 418 is rotatably coupled at one end to the top ring 186b of the coupling 186 and secured at the other end thereof to a second coupling 188 mounted on the twisted pair 172 and thus, rotates as it advances along the pair when the driving rod 476 is linearly reciprocated by the piston 170. A central tube 178 extends from the lower portion of the outer tube, up through the driving member 476 and piston 170 and is connected to the controller 452 to allow the particles milled by the milling tool 418 to be removed from the vessel by suction. An access tube 190 is also provided to allow the upper portion of the tube 412 to be pressurized in order to reciprocate the piston 170. A second tube 191 is provided to allow the balloon 496 to be inflated by the infusion of air or saline.

To drive the piston 170, the upper portion of the tube 412 is pressurized by air or saline solution supplied by the controller 452 via the access tube 190. The air is alternatively withdrawn and applied into the upper portion and provides the force for reciprocating the piston. The piston 170 in turn linearly drives the driving rod 476 to extend beyond the milling tool 418 so that the coupling 188 rotates around the twisted pair 172 as the pair advances, thereby causing the milling tool 418 to rotate. When the piston 170 is drawn into the tube 412, the engagement between the coupling 188 and the twisted pair 172 allows the milling tool 484 to rotate in the opposite direction. As shown in FIGS. 9a to 9c, the forced air piston drive mechanism is replaced by an electromagnetic drive mechanism, the operation of which is known in the art and will not be described here.

FIGS. 10a to 10f show the milling tool 418 and the twisted pair 172 in more detail. The twisted pair 172 is also provided with abutment pegs 184 for limiting the linear movement of the driving rod 476 with respect to the milling tool 418 and for providing an abutment means. The milling tool 418 can also include an "umbrella" 180 secured to the driving rod 476 and capable of opening upon movement of the twisted pair 172 towards the milling tool 418. The umbrella 180 is provided with teeth 182 for cutting the deposit and is rotatable with the milling tool 418. Thus, the milling tool 418 can provide further cutting of the deposit in a plane substantially perpendicular to the axis of the driving rod 476. To expand the edges of the milling tool 418, the abutment pegs 184 are brought into further engagement with the tool 418 thereby compressing the tool since the milling tool is secured to the removable rings 186b at one end.

Referring to FIGS. 12 and 13, still yet further embodiment of the angioplasty apparatus are shown. In these embodiments, the drive mechanism is similar to that shown in FIGS. 8 and 9 except the milling tool 418 is secured to the reciprocating driving rod 476 rather than being rotatably secured to the base 430 by the coupling 186. Thus, in these embodiments, the milling tool 418 is linearly reciprocated with the driving rod 476 and alternately rotates in opposite directions. This allows the milling tool 418 to extend further into the vessel unlike the milling tool 418 in the embodiment of FIGS. 8 and 9. Furthermore, the milling tool 418 can be compressed so that the outer edges extend beyond the outer edge of the tube 412 by moving the milling tool 418 so that it abuts against the base plate 430 while still being rotated. It should be apparent that each of the above embodiments described include a sensing device similar to that described in FIG. 1 for monitoring the removal of deposits from vessel tissue. It should also be appreciated that a balloon is used to secure the apparatus in the vessel and that an appropriate controller is used to provide forced air, an electrical power supply or simply suction depending on which embodiment of the angioplasty aparatus is being used.

I claim:

1. An angioplasty apparatus for removing abnormal deposits such as atheromatic plaque from the interior walls of blood vessels and the like comprising:
   a hollow elongate flexible member having one end for insertion into a vessel;
   a driving member coupled to said elongate flexible member and extending forwardly of the one end of said flexible member;
   milling means connected to said driving member exterior to said elongate member;
   drive means in communication with said driving member for actuating said driving member, said driving member rotating said milling means alternately in opposite directions to engage and mill said deposits upon actuation thereof by said drive means;
   suction means in communication with said elongate flexible member for withdrawing milled particles of said deposit from said vessel and into said elongate flexible member; and
   sensing means located on said elongate flexible member for effecting electrical coupling between said vessel and said milling means, said sensing means sensing when said milling means has removed said deposit from the interior walls of said vessel.

2. An angioplasty apparatus as defined in claim 1 wherein said sensing means includes a pair of resistive circuits, one of said resistive circuits for engaging with a healthy vessel section and the other of said resistive circuits being coupled to said milling means;
   a voltage source for energizing said resistive circuits to allow a current to flow therein; and
   comparing means for comparing the electrical resistance in said resistive circuits to detect when said deposit is removed from the interior walls of said vessel.

3. An angioplasty apparatus as defined in claim 2 further comprising an inflatable member engaged with the outer sides of said elongate flexible member and being operable to expand in order to engage with said healthy vessel section to hold securely said apparatus in position in said vessel.

4. An angioplasty apparatus as defined in claim 3 wherein said one resistive circuit is connected to said inflatable member , said one resistive circuit contacting said healthy vessel section upon inflation of said inflatable member.

5. An angioplasty apparatus as defined in claim 1, further comprising linear displacement means disposed on said driving member for allowing said milling means to be displaced linearly along said driving member while alternately rotating in opposite directions.

6. An angioplasty apparatus as defined in claim 5 wherein said drive means is a linear actuator and said linear displacement means is formed from a twisted wire pair, said milling means being secured to said twisted wire pair by a coupling, said twisted wire pair permitting rotation of said milling means as said linear actuator is reciprocated to advance linearly said milling means along said twisted wire pair.

7. An angioplasty apparatus as defined in claim 6 whereins aid linear actuator is a piston and cylinder arrangement in communication with said driving member, said driving member being reciprocated upon reciprocation of said piston in said cylinder.

8. An angioplasty apparatus as defined in claim 7 wherein said piston is reciprocated in said cylinder by the introduction and withdrawal of a suitable fluid into said elongate flexible member.

9. An angioplasty apparatus as defined in claim 7 wherein said piston is formed from magnetic material and wherein said cylinder is defined by said elongate flexible member, said drive means includes a magnetizable body in communication with an alternating current power supply, said magnetizable body being in communication with said piston and being operable to reciprocate said piston upon the energization thereof by said power supply.

10. An angioplasty apparatus as defined in claim 6 wherein said milling means includes a flexible leaf shaped milling tool having milling flutes provided thereon.

11. An angioplasty apparatus as defined in claim 10 wherein said milling tool further includes a flexible cutting implement movable from an inoperative position to an operative position, said implement being positioned at the distal end of said milling tool and being rotatable to provide cutting of said deposit in a plane substantially perpendicular to the axis of rotation of said milling tool.

12. An angioplasty apparatus as defined in claim 1 wherein said milling means is formed from a flexible leaf-shaped material and is coupled securely at one end to the distal end of said driving member, said driving member also being linearly displaceable with respect to said elongate flexible member to abut the proximal end of said milling means against the one end of said elongate flexible member , said milling means expanding in the radial dimension upon abutment of said milling means against said elongate flexible member.

13. An angioplasty apparatus as defined in claim 12 wherein said drive means includes an inner member having an open inner end and being disposed in said elongate flexible member to define first and second passages;
   a turbine disposed in said inner member and being secured to said driving member, said turbine being rotatable in said inner member to rotate said driving member; and
   an air supply means for supplying air alternatively into one of said first and second passages and through said turbine to rotate said turbine alternately in opposite directions.

14. An angioplasty apparatus as defined in claim 12 wherein said drive means includes a divider disposed in said elongate member for partitioning a portion of said elongate flexible member into a pair of substantially parallel passages;
- a pair of mating right-angled gears coupled to said driving member and disposed in the other portion of said elongate flexible member, said mating gears extending across said passages; and
- an air supply means for supplying air alternatively into one of said parallel passages and across said gears to rotate said gears alternately in opposite directions.

15. An angioplasty apparatus as defined in claim 12 wherein said drive means includes a pair of electromagnets located on opposite sides of said elongate member;
- a magnetic rotor coupled to said driving member and positioned between said electromagnets; and
- an alternating power supply for energizing said electro magnets, said electro magnets rotating said rotor alternately in opposite directions upon the energization thereof by said power supply.

16. An angioplasty apparatus as defined in claim 1 wherein said suction means includes a vacuum pump in communication with an end of said elongate flexible member opposite said one end, said vacuum pump withdrawing said milled particles from said flexible member.

* * * * *